(12) United States Patent
Merril et al.

(10) Patent No.: US 11,911,345 B2
(45) Date of Patent: Feb. 27, 2024

(54) PHAGE DISPENSING SYSTEM

(71) Applicant: Adaptive Phage Therapeutics, Inc., Gaithersburg, MD (US)

(72) Inventors: Carl Merril, Bethesda, MD (US); Greg Merril, Bethesda, MD (US)

(73) Assignee: Adaptive Phage Therapeutics, Inc., Gaithersburg, MD (US)

( * ) Notice: Subject to any disclaimer, the term of this patent is extended or adjusted under 35 U.S.C. 154(b) by 62 days.

(21) Appl. No.: 16/896,718

(22) PCT Filed: Dec. 10, 2018

(86) PCT No.: PCT/US2018/064645
§ 371 (c)(1),
(2) Date: Jun. 9, 2020

(87) PCT Pub. No.: WO2019/118310
PCT Pub. Date: Jun. 20, 2019

(65) Prior Publication Data
US 2020/0375850 A1 Dec. 3, 2020

Related U.S. Application Data

(60) Provisional application No. 62/597,008, filed on Dec. 11, 2017.

(51) Int. Cl.
*A61J 7/00* (2006.01)
*G16H 20/13* (2018.01)
(Continued)

(52) U.S. Cl.
CPC .............. *A61J 7/0076* (2013.01); *A61J 1/06* (2013.01); *A61K 35/76* (2013.01); *B65G 1/1371* (2013.01);
(Continued)

(58) Field of Classification Search
CPC .... G07F 17/0092; G16H 20/13; G16H 40/20; G16H 10/40; A61K 35/76
See application file for complete search history.

(56) References Cited

U.S. PATENT DOCUMENTS

| 4,847,764 A |   | 7/1989 | Halvorson |
| 5,921,102 A | * | 7/1999 | Vago ........................ F25D 25/00 |
|  |  |  | 62/51.1 |

(Continued)

FOREIGN PATENT DOCUMENTS

| EP | 2269560 A1 | 1/2011 |
| EP | 3724886 B1 | 10/2022 |

(Continued)

OTHER PUBLICATIONS

Fortier et al., "Phage Production and Maintenance of Stocks, Including Expected Stock Lifetimes", DNA Repair Protocols. Methods in Molecular Biology, vol. 501, pp. 203-219 (2009).

(Continued)

*Primary Examiner* — Timothy R Waggoner
(74) *Attorney, Agent, or Firm* — Edell, Shapiro & Finnan, LLC

(57) ABSTRACT

A phage dispensing system comprises a user interface, a phage treatment computing system, a phage laboratory, and a phage dispensing apparatus, including a dispensing kiosk. The user interface allows a treating physician to request testing of a patient sample by the phage laboratory to identify a phage mixture treatment. The phage computing system arranges shipping of the sample and provision of the identified phage mixture treatment to a dispensing apparatus located near the patient. The dispensing apparatus has a stock of phage vials which are used to prepare and dispense doses of the identified phage mixture treatment.

28 Claims, 2 Drawing Sheets

(51) Int. Cl.
*G16H 40/20* (2018.01)
*G16H 10/40* (2018.01)
*A61J 1/06* (2006.01)
*A61K 35/76* (2015.01)
*B65G 1/137* (2006.01)
*B65G 61/00* (2006.01)

(52) U.S. Cl.
CPC ............ *G16H 10/40* (2018.01); *G16H 20/13* (2018.01); *G16H 40/20* (2018.01); *A61J 2200/70* (2013.01); *A61J 2205/10* (2013.01); *A61J 2205/60* (2013.01); *B65G 61/00* (2013.01)

(56) References Cited

U.S. PATENT DOCUMENTS

| | | | |
|---|---|---|---|
| 6,032,155 | A | 2/2000 | Juerga |
| 6,175,779 | B1 | 1/2001 | Barrett |
| 8,065,035 | B2 | 11/2011 | Ross et al. |
| 2003/0180319 | A1* | 9/2003 | Rapson ............... A61K 39/12 435/235.1 |
| 2004/0236463 | A1* | 11/2004 | Weselak ............ G11B 15/6835 700/214 |
| 2005/0247782 | A1 | 11/2005 | Ambartsoumian |
| 2009/0294521 | A1* | 12/2009 | de La Huerga ......... A61J 1/035 235/375 |
| 2011/0315588 | A1 | 12/2011 | Ross et al. |
| 2013/0066465 | A1* | 3/2013 | Har-Noy ............. G07F 17/0092 700/236 |
| 2013/0151005 | A1 | 6/2013 | Gerold et al. |
| 2015/0069080 | A1 | 3/2015 | DiMartino et al. |
| 2017/0057682 | A1 | 3/2017 | Chudy |
| 2017/0136452 | A1 | 5/2017 | Niles et al. |

FOREIGN PATENT DOCUMENTS

| | | |
|---|---|---|
| JP | 7-500521 A | 1/1995 |
| JP | 10-500789 A | 1/1998 |
| JP | 2004-287833 A | 10/2004 |
| JP | 2005-514965 A | 5/2005 |
| JP | 2009541746 A | 11/2009 |
| JP | 2015512384 A | 4/2015 |
| WO | 94/04415 A1 | 3/1994 |
| WO | 95/25423 A2 | 9/1995 |
| WO | 02/095675 A1 | 11/2002 |
| WO | 2008042481 A2 | 4/2008 |
| WO | 2013141730 A1 | 9/2013 |
| WO | 2014/015186 A1 | 1/2014 |
| WO | 2017062986 A1 | 4/2017 |

OTHER PUBLICATIONS

International Search Report and Written Opinion dated Mar. 22, 2019 and received in PCT/US2018/064645.
International Search Report and Written Opinion dated May 14, 2019 and received in PCT/US2018/064645.
Malik, "Formulation, Stabilisation and Encapsulation of Bacteriophage for Phage Therapy", Advances in Colloid and Interface Science, vol. 249, pp. 100-133, (2017).
Wikipedia: The Free Encyclopedia: "Phage Therapy", Retrieved from the Internet: URL: https://en.wikipedia.org/w/index.php?title=Phage_therapy&oldid=813234449 (2017).
EPO Office Action dated Nov. 9, 2021 received in corresponding EP Application 18830103.0.
EPO Office Action Dated Apr. 12, 2021 received in corresponding EP Application 18830103.0.
International Search Report and Written Opinion dated Jun. 25, 2020 and received in PCT/US18/64645.
Japanese Office Action and English Translation dated Oct. 18, 2022 received in corresponding JP Application 2020-531605.
Extended European Search Report in corresponding EP Application No. 22199498.1, dated Feb. 7, 2023, 14 pages.
EPO Office Action dated Dec. 22, 2023 received in corresponding EP Application 22199498.1, 6 pages.
Japanese Office Action and English Translation dated Dec. 15, 2023 received in corresponding JP Application 2023-003707, 7 pages.

* cited by examiner

PHAGE DISPENSING SYSTEM

CROSS-REFERENCE TO RELATED APPLICATIONS

This application is a § 371 National Stage Application of PCT/US18/64645 filed on Dec. 10, 2018, which claims priority to USSN 62/597,008 filed on Dec. 11, 2017, both of which are hereby incorporated by reference in their entirety.

BACKGROUND OF THE INVENTION

Field of the Invention

The invention relates to automated dispensing systems for pharmaceutical compositions.

Discussion of the Related Art

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Multiple drug resistant (MDR) bacteria are emerging at an alarming rate. Currently, it is estimated that at least 2 million infections are caused by MDR organisms every year in the United States leading to approximately 23,000 deaths. Moreover, it is believed that genetic engineering and synthetic biology may also lead to the generation of additional highly virulent microorganisms.

For example, *Staphylococcus aureus* are gram positive bacteria that can cause skin and soft tissue infections (SSTI), pneumonia, necrotizing fasciitis, and blood stream infections. Methicillin resistant *S. aureus* ("MRSA") is an MDR organism of great concern in the clinical setting as MRSA is responsible for over 80,000 invasive infections, close to 12,000 related deaths, and is the primary cause of hospital acquired infections. Additionally, the World Health Organization (WHO) has identified MRSA as organisms of international concern.

In view of the potential threat of rapidly occurring and spreading virulent microorganisms and antimicrobial resistance, alternative clinical treatments against bacterial infection are being developed. One such potential treatment for MDR infections involves the use of phage. Bacteriophages ("phages") are a diverse set of viruses that replicate within and can kill specific bacterial hosts. The possibility of harnessing phages as an antibacterial was investigated following their initial isolation early in the 20th century, and they have been used clinically as antibacterial agents in some countries with some success. Notwithstanding, phage therapy was largely abandoned in the U.S. after the discovery of penicillin, and only recently has interest in phage therapeutics been renewed.

The successful therapeutic use of phage depends on the ability to administer a phage strain that can kill or inhibit the growth of a bacterial isolate associated with an infection. In addition, given the mutation rate of bacteria and the narrow host range associated with phage strains, a phage strain that is initially effective as an antibacterial agent can quickly become ineffective during clinical treatment as the initial target bacterial host either mutates or is eliminated and is naturally replaced by one or more emergent bacterial strains that are resistant to the initial phage employed as an antibacterial agent.

Empirical laboratory techniques have been developed to screen for phage susceptibility on bacterial strains. However, these techniques are time consuming and are dependent upon obtaining a bacterial growth curve for each specific strain of bacterium. For example, phage stains are currently screened for their capacity to lyse (kill) or inhibit bacterial growth by testing individual phage strains against a specific patient's bacterial isolate using either liquid cultures or bacterial lawns grown on agar media. This growth requirement cannot be quickened and susceptibility results are generated only after hours, and in some cases, days of screening. Further such screening is typically performed at specialized laboratories remote from the patient. Accordingly patient samples must be suitably prepared and shipped to the testing laboratory, and then on identification of a potential phage treatment (from the susceptibility results), a suitable pharmaceutical composition comprising the identified phage (or phages) must be suitably prepared and shipped to the treating physician for subsequent administration to the patient. This delay in obtaining susceptibility results and subsequent dispensing and delivery leads to delay of treatment and complications for a patient suffering from a systemic bacterial infection.

Thus, there is a need to develop a dispensing system for delivering phage based pharmaceutical compositions to patients, or to at least provide a useful alternative to current dispensing systems.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

Embodiments of the invention relate to a phage dispensing system and method of operation to identify a phage mixture treatment for a patient and then to prepare and dispense the dose of the phage mixture treatment at the point of care. The system speeds up the process of both identifying a phage mixture treatment from a patient sample, and the dispensing one or more doses of the identified phage mixture treatment.

According to a first aspect there is provided a phage dispensing apparatus comprising:
  a computing apparatus comprising one or more processors; a memory; a communications interface, a display and one or more programs, wherein the one or more programs are stored in the memory and configured to be executed by the one or more processors, the one or more programs are configured to receive information regarding a patient and a phage mixture treatment for the patient;
  a storage portion comprising a plurality of vials containing at least one phage;
  a preparation portion;
  a dispensing portion;
  and one or more robotic systems controlled by the computing apparatus and configured to remove one or more vials from the storage portion, and move the one or more vials to the preparation portion, mix the one or more vials to a generate a pharmaceutically acceptable phage mixture treatment, and to dispense one or more doses of the pharmaceutically acceptable phage mixture treatment The storage portion may comprise a plurality of single dose phage vials and the storage portion is kept at between −40° C. and −90° C.

The computing apparatus may be is configured to maintain an inventory of the plurality of vials in the storage portion, and a sensor is configured to detect removal of a vial from the storage portion, and on detection the inventory is updated, and if an inventory level of a stored phage is less than a threshold amount, a request for new phage stock is transmitted to a supplier via the communications interface.

The computing apparatus may monitor preparation of one of more does of the phage mixture treatment, and an alert is generated by the communications interface when one or more doses of the phage mixture treatment is prepared and ready for dispensing, and the computing apparatus stores a database of authorized users, and is configured to only dispense the one or more doses of the phage mixture treatment to an authorized user.

The storage portion may further comprise a plurality of pre-prepared phage mixture treatment vials comprising multiple phages with efficacy against one of a selected group of multi drug resistant bacteria, and preparing one or more doses of the phage mixture comprises selecting one or more pre-prepared phage mixture treatment vials from the storage portion and defrosting the selected one or more pre-prepared phage mixture treatment vials.

According to a second aspect there is provided a therapeutic phage storage and dispensing apparatus comprising:
  (a) a temperature controlled storage box containing a plurality of sealed vials each of which contains a sterile-filled preparation with a volume of between 1 ml and 50 ml, and each preparation comprise one or more strains of purified phage; and
  (b) an electronic catalogue apparatus configured to track the inventory of the plurality of vials stored in the temperature controlled storage box.

Each preparation may comprise $10^6$ to $10^{14}$ plaque-forming unit (PFU) of one or more phages. Each vial may be an ampule Each vial may comprise an identification tag, and the electronic catalogue apparatus comprises one or more sensors to detect addition and removal of each vial to and from the temperature controlled storage box using the identification tag, and is further configured to record the location of each vial within the temperature controlled storage box. The electronic catalogue apparatus may further comprise a robotic apparatus configured to move a vial to and from a storage location within the temperature controlled box According to a third aspect there is provided a computing apparatus comprising:
  one or more processors; a memory; a communications interface, a display and one or more programs, wherein the one or more programs are stored in the memory and configured to be executed by the one or more processors, the one or more programs are configured to:
  (a) receive information regarding a patient sample via a user interface, the information comprising a patient sample location, a patient identifier, and a treatment location;
  (b) arranging transportation of the patient sample to a phage testing laboratory using the received information;
  (c) receiving one or more test and/or analysis results from the phage testing laboratory and generating phage mixture treatment comprising one of more phages from the phage testing laboratory;
  (d) sending the phage mixture treatment and the patient identifier to a phage dispensing apparatus for dispensing one or more doses of the phage mixture treatment to the patient.

Arranging transportation may comprise identifying the nearest phage testing laboratory that has capacity to receive and test the patient sample, booking a transportation service to transport the patient sample from a sample pickup location at a sample pickup time, and sending information to the user interface to allow a user to print a shipping label, and informing the user of the sample pickup time and pickup location.

The computer apparatus may be further configured to receive a request for new phage stock from a phage dispensing apparatus, and arranging transportation of requested new phage stock to the phage dispensing apparatus.

According to a fourth aspect there is provided a computer implemented method for dispensing one or more doses of a phage mixture treatment, the method comprising:
  (a) receiving information regarding a patient sample via a user interface, the information comprising a patient sample location, a patient identifier, and a treatment location;
  (b) arranging transportation of the patient sample to a phage testing laboratory using the received information;
  (c) testing and/or analyzing the patient sample to identify a phage mixture treatment comprising one of more phages;
  (d) sending the phage mixture treatment to a phage dispensing apparatus;
  (e) preparing one or more doses of the phage mixture treatment using one or more phage vials stored by the phage dispensing apparatus;
  (f) dispensing the one or more doses of the phage mixture treatment.

Arranging transportation may comprise identifying the nearest phage testing laboratory that has capacity to receive and test the patient sample, booking a transportation service to transport the patient sample from a sample pickup location at a sample pickup time, and sending information to the user interface to allow a user to print a shipping label, and informing the user of the sample pickup time and pickup location.

Various methods may be used to test and/or analyze the patient sample to identify the phage mixture treatment. These may comprise plaque assay or using a photometric assay. The phage mixture treatment may comprise a plurality of phages. These may have different host ranges, and may act synergistically with one another. Each phage in the phage mixture may either:
  (i) cause a delay in bacterial growth;
  (ii) inhibit or prevent the appearance of phage-resistant bacterial growth;
  (iii) cause the bacteria to less virulent;
  (iv) cause the bacteria to regain sensitivity to one or more drugs; and/or
  (v) cause the bacteria to display reduced fitness for growth in the subject.

The phage dispensing apparatus may comprise a plurality of single dose phage vials stored in a storage portion kept at between −40° C. and −85° C., and preparing one or more doses of the phage mixture comprises selecting one or more single dose phage vials from the storage portion according to the received phage mixture treatment, defrosting the selected one or more single dose phage vials and mixing to generate a phage mixture treatment. The doses of the phage mixture treatment may be formulated as a pharmaceutically acceptable composition.

As each vial is removed from the storage portion, an inventory may be updated, and if an inventory level of a stored phage is less than a threshold amount, a request for new phage stock is transmitted to a supplier.

An alert may be generated when the phage mixture treatment is prepared and ready for dispensing, and the prepared phage mixture treatment is only dispensed to an authorized user.

The phage dispensing apparatus may also comprise a plurality of pre-prepared phage mixture treatment vials comprising multiple phages with efficacy against one of a selected group of multi drug resistant bacteria. Preparing one or more doses of the phage mixture comprises selecting one or more pre-prepared phage mixture treatment vials from the storage portion and defrosting the selected one or more pre-prepared phage mixture treatment vials.

According to a fifth aspect there is provided a phage dispensing system comprising:
(a) a phage dispensing apparatus comprising a storage portion comprising a plurality of vials containing at least one phage, a preparation portion, a dispensing portion, and one or more robotic systems configured to remove one or more vials from the storage portion, and moving the one or more vials to the preparation portion, mix the one or more portions to a generate a pharmaceutically acceptable phage mixture treatment, and to dispense one or more doses of the pharmaceutically acceptable phage mixture treatment; and
(b) one or more processors; memory; and one or more programs, wherein the one or more programs are stored in the memory and configured to be executed by the one or more processors, the one or more programs including instructions for carrying out the method of the fourth aspect.

BRIEF DESCRIPTION OF THE FIGURES

The objects and features of the invention can be better understood with reference to the following detailed description and accompanying drawings.

Like reference numbers and designations in the various drawings indicate like elements.

DETAILED DESCRIPTION

Figure 1:
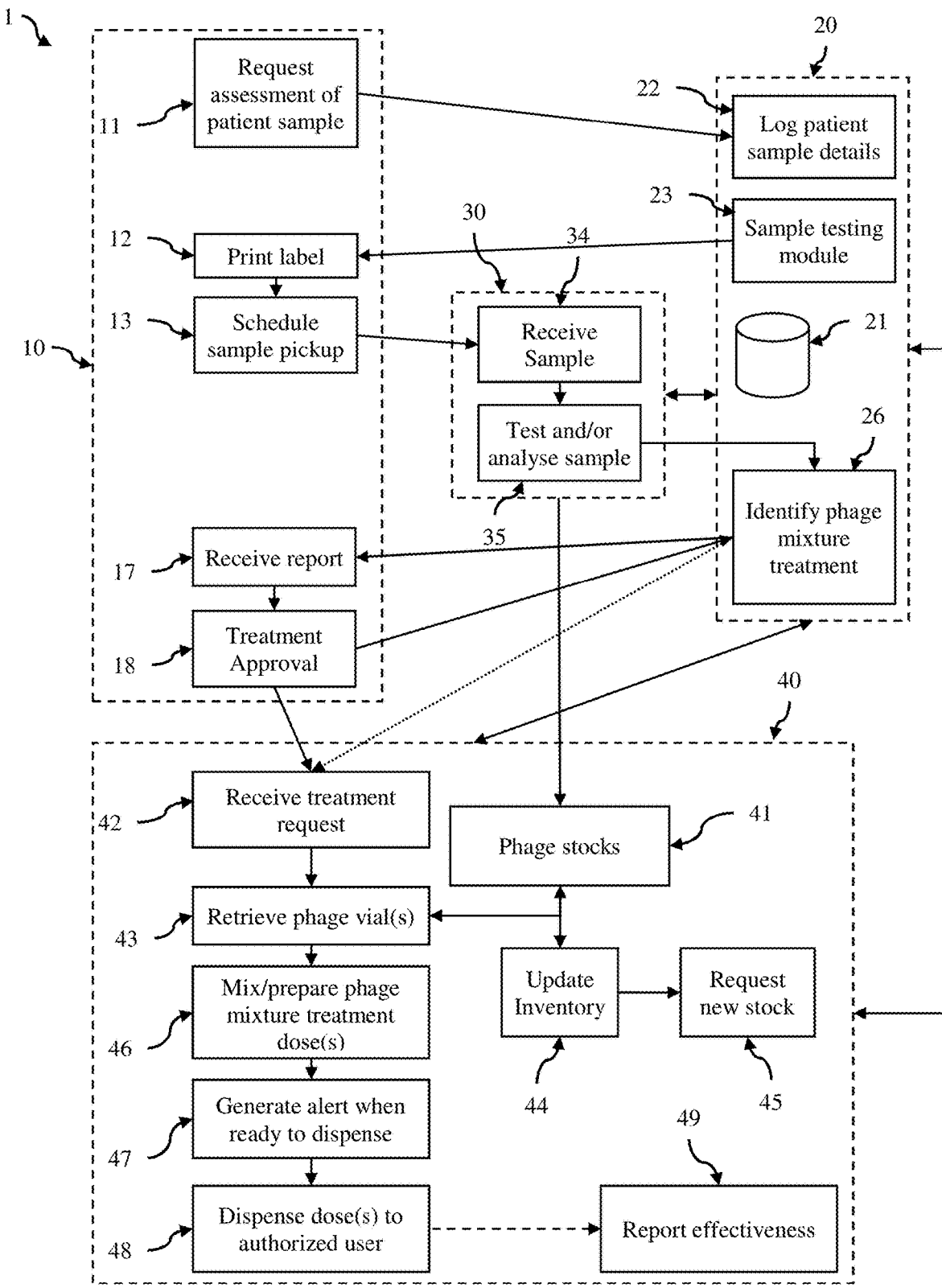
FIG. 1 is a schematic diagram and operational flowchart of an embodiment of a Phage Dispensing System.

The following definitions are provided for specific terms which are used in the following written description.

Definitions

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules. "A phage mixture" can mean at least one phage mixture, as well as a plurality of phage mixtures, i.e., more than one phage mixture. As understood by one of skill in the art, the term "phage" can be used to refer to a single phage or more than one phage.

The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention.

As used herein, a "subject" is a vertebrate, preferably a mammal, more preferably a human. Mammals include, but are not limited to, murines, simians, humans, farm animals, sport animals, and pets. In other preferred embodiments, the "subject" is a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), or an ape (e.g., gorilla, chimpanzee, orangutan, gibbon). In other embodiments, non-human mammals, especially mammals that are conventionally used as models for demonstrating therapeutic efficacy in humans (e.g., murine, primate, porcine, canine, or rabbit animals) may be employed. Preferably, a "subject" encompasses any organisms, e.g., any animal or human, that may be suffering from a bacterial infection, particularly an infection caused by a multiple drug resistant bacterium.

As understood herein, a "subject in need thereof" includes any human or animal suffering from a bacterial infection, including but not limited to a multiple drug resistant bacterial infection. Indeed, while it is contemplated herein that the methods may be used to target a specific pathogenic species, the method can also be used against essentially all human and/or animal bacterial pathogens, including but not limited to multiple drug resistant bacterial pathogens. Thus, in a particular embodiment, by employing the methods of the present invention, one of skill in the art can design and create personalized phage mixtures against many different clinically relevant bacterial pathogens, including multiple drug resistant (MDR) bacterial pathogens.

As understood herein, an "effective amount" of a pharmaceutical composition refers to an amount of the composition suitable to elicit a therapeutically beneficial response in the subject, e.g., eradicating a bacterial pathogen in the subject. Such response may include e.g., preventing, ameliorating, treating, inhibiting, and/or reducing one of more pathological conditions associated with a bacterial infection.

The term "dose" or "dosage" as used herein refers to physically discrete units suitable for administration to a subject, each dosage containing a predetermined quantity of the active pharmaceutical ingredient calculated to produce a desired response.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value. Unless otherwise stated, the term "about" means within an acceptable error range for the particular value, such as ±1-20%, preferably ±1-10% and more preferably ±1-5%. In even further embodiments, "about" should be understood to mean+/−5%.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Where used herein, the term "and/or" when used in a list of two or more items means that any one of the listed characteristics can be present, or any combination of two or more of the listed characteristics can be present. For example, if a composition is described as containing characteristics A, B, and/or C, the composition can contain A feature alone; B alone; C alone; A and B in combination; A and C in combination; B and C in combination; or A, B, and C in combination.

The term "phage sensitive" or "sensitivity profile" means a bacterial strain that is sensitive to infection and/or killing by phage and/or in growth inhibition.

The term "phage insensitive" or "phage resistant" or "phage resistance" or "resistant profile" is understood to mean a bacterial strain that is insensitive, and preferably highly insensitive to infection and/or killing by phage and/or growth inhibition.

The term "intermediate phage sensitive" is understood to mean a bacterial strain that exhibits a sensitivity to infection by phage that is in between the sensitivity of phage sensitive and phage insensitive strains.

As used herein, "predictive patterns" are genomic patterns identified in the plurality of bacterial strains and/or in the plurality of phage strains that are associated correlate with a "sensitivity profile", "resistant profile", or "intermediate sensitivity profile" of a bacterium.

As used herein, a "phage-host specificity profile" is used interchangeably with a "phage-host sensitivity profile" and comprises data relating to a bacterium's sensitivity or resistance to a plurality of different phage. The phage-host specificity profile can be experimentally derived, computationally predicted, or some combination.

A "therapeutic phage mixture", "therapeutically effective phage mixture", "phage mixture" or like terms as used herein are understood to refer to a composition comprising a plurality of phage which can provide a clinically beneficial treatment for a bacterial infection when administered to a subject in need thereof. In preferred embodiments, the phage mixture comprises phage having different sensitivity profiles; although a phage mixture can also comprise a single type of phage. Preferably, therapeutically effective phage mixtures are capable of infecting the infective parent bacterial strain as well as the emerging resistant bacterial strains that may grow out after elimination of the parent bacterial strain.

As used herein, the term "composition" encompasses "phage mixtures" as disclosed herein which include, but are not limited to, pharmaceutical compositions comprising a plurality of purified phages. "Pharmaceutical compositions" are familiar to one of skill in the art and typically comprise active pharmaceutical ingredients formulated in combination with inactive ingredients selected from a variety of conventional pharmaceutically acceptable excipients, carriers, buffers, and/or diluents. The term "pharmaceutically acceptable" is used to refer to a non-toxic material that is compatible with a biological system such as a cell, cell culture, tissue, or organism. Examples of pharmaceutically acceptable excipients, carriers, buffers, and/or diluents are familiar to one of skill in the art and can be found, e.g., in *Remington's Pharmaceutical Sciences* (latest edition), Mack Publishing Company, Easton, Pa. For example, pharmaceutically acceptable excipients include, but are not limited to, wetting or emulsifying agents, pH buffering substances, binders, stabilizers, preservatives, bulking agents, adsorbents, disinfectants, detergents, sugar alcohols, gelling or viscosity enhancing additives, flavoring agents, and colors. Pharmaceutically acceptable carriers include macromolecules such as proteins, polysaccharides, polylactic acids, polyglycolic acids, polymeric amino acids, amino acid copolymers, trehalose, lipid aggregates (such as oil droplets or liposomes), and inactive virus particles. Pharmaceutically acceptable diluents include, but are not limited to, water, saline, and glycerol.

Bacteria to be treated using the phage mixture treatment and compositions described herein include any bacterial pathogen that poses a health threat to a subject. These bacterial include, but are not limited to the "ESKAPE" pathogens (*Enterococcus faecium, Staphylococcus aureus, Klebsiella pneumonia, Acinetobacter baumannii, Pseudomonas aeruginosa,* and *Enterobacter* sp), which are often nosocomial in nature and can cause severe local and systemic infections. Among the ESKAPE pathogens, *A. baumannii* is a Gram-negative, capsulated, opportunistic pathogen that is easily spread in hospital intensive care units. Many *A. baumannii* clinical isolates are also MDR, which severely restricts the available treatment options, with untreatable infections in traumatic wounds often resulting in prolonged healing times, the need for extensive surgical debridement, and in some cases the further or complete amputation of limbs. Further preferred bacteria strains include *G. mellonella.*

One of skill in the art will appreciate that bacteria subject to the method described herein include, but are not limited to, multidrug resistant bacterial strains. As understood herein, the terms, "multidrug resistant", "multiple drug resistant", "multiple drug resistance" (MDR) and like terms may be used interchangeably herein, and are familiar to one of skill in the art, i.e., a multiple drug resistant bacterium is an organism that demonstrates resistance to multiple antibacterial drugs, e.g., antibiotics.

In preferred embodiments, examples of MDR bacteria are methicillin resistant *S. aureus* (MRSA) and vancomycin-resistant Enterococci (VRE) vancomycin-resistant Enterococci (VRE).

As understood herein, the term "diverse sources" includes a wide variety of different places where phage may be found in the environment including, but not limited to, any place where bacteria are likely to thrive. In fact, phage are universally abundant in the environment, making the isolation of new phage very straightforward. The primary factors affecting the successful isolation of such phage are the availability of a robust collection of clinically relevant bacterial pathogens to serve as hosts, and access to diverse environmental sampling sites.

Screening methods can be employed to rapidly isolate and amplify lytic phage specific to bacterial pathogen(s) of interest and their therapeutic potential can be investigated. Possible sources include, e.g., natural sources in the environment such as soil, sea water, animal intestines (e.g., human intestines), as well as man-made sources such as untreated sewage water and water from waste water treatment plants. Clinical samples from infected patients may also serve as a source of phage. In one embodiment, diverse sources of phage may be selected from the group consisting of soil, water from waste water treatment plants, raw sewage, sea water, and animal and human intestines. Moreover, phage may be sourced anywhere from a variety of diverse locations around the globe, e.g., within the US and internationally. Preferably, phage can be isolated from diverse environmental sources, including soil, water treatment plants, raw sewage, sea water, lakes, rivers, streams, standing cesspools, animal and human intestines or fecal matter, organic substrates, biofilms, or medical/hospital sources.

As understood herein, the concept of "distinct and overlapping bacterial host ranges" refers to bacterial host ranges particular for a given phage, but which may overlap with the distinct host range of a different phage. For example, the concept is similar to a collection of venn diagrams; each circle can represent an individual phage's host range, which may intersect with one or more other phage's host range.

As used herein, the term "purified" refers to a preparation that is substantially free of unwanted substances in the composition, including, but not limited to biological materials e.g., toxins, such as for example, endotoxins, nucleic acids, proteins, carbohydrates, lipids, or subcellular organelles, and/or other impurities, e.g., metals or other trace elements, that might interfere with the effectiveness of the mixture. As used herein, terms like "high titer and high purity", and "very high titer and very high purity" refers to degrees of purity and titer that are familiar to one of skill in the art.

As used herein, the term "vial" encompasses a range of containers which can be used to contain or store an individual phage in solution or a phage mixture and include lids. Vials may be single dose or multi dose containers. Single dose containers may be sealed including ampules and other hermetically sealed vials. Multi dose containers may store phage at a specific concentration or comprise a partitioned interior. Vials may be made of suitable glasses, plastics, composites or metal, that can store the phage in a viable state for an extended period of time, including at low temperatures such as −80° C. or −90° C.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

Phage Dispensing System

With reference to FIG. 1 there is shown a schematic diagram and operational flowchart of an embodiment of a Phage Dispensing System 1. The Phage Dispensing system 1 is configured to control and coordinate the interaction of a treating physician, a phage laboratory which tests a patient sample and recommends a phage mixture treatment, and actual dispensing of one or more doses of the phage mixture treatment to a clinician (eg pharmacist, nurse or the treating physician). In this embodiment the Phage Dispensing System 1 comprises a user interface 10, a phage treatment computing system 20, a phage laboratory 30, and a phage dispensing apparatus 40, such as a dispensing kiosk.

Phage Treatment Computing System and User Interface

When a treating physician identifies a patient who may benefit from a phage based treatment, they access the user interface 10 to request assessment of a patient sample 11 by the phage laboratory 30. The user interface is configured to collect a patient identifier as well as any other relevant information regarding the patient and their condition, as well as logistical details such as patient sample location, and where the patient and physician are located or where they are to be treated. The user interface may also be configured to interact with other computing systems such as patient records systems to assist in collection of any required information. Similarly for a registered or previous user, the user interface may prefill or use existing details (eg addresses) already known to the phage treatment system 20. The treating physician user interface may be a web browser or a local application running on a local computing device associated with the physician such as a desktop computer, laptop computer, computing tablet or smart phone. The user interface is configured to send the data to the phage treatment computing system 20, over a communication link, such as wired or wireless link, including over a public network such as the internet. The data request may be encrypted to ensure patient confidentiality. It will also be recognised that data entry to the user interface may be via the treating physician or another person with knowledge of relevant information (eg nurse or administrator).

The phage treatment computing system 20 comprises a database 21 and a communications interface that receives the request and logs the patient sample details 22 into database 21. A sample testing module 23 determines a suitable phage laboratory 30 to test the patient sample and coordinates the transportation of the sample from the initial test sample location to the phage laboratory. In some embodiments there may be multiple phage laboratories 30 distributed across a service area. The sample testing module 23 can determine the geographic location of the test sample location which may be the treating physician location, the patient location, or a patient sample collection facility, and determine the nearest phage testing laboratory 30 that has capacity to receive and test the sample. The sample testing module 23 also determines a courier or transportation service that can efficiently transport the patient sample to the phage testing laboratory 30. The phage treatment computing system 20 may be co-located at a phage laboratory 30 or be a distributed system including cloud based and datacentre based implementations, in which users can log in and interact with the system from multiple locations.

In some embodiments the sample testing module 23 provides printing details and the user interface 10 is then used to print a shipping label for the patient sample 12 and a sample pickup time is scheduled with a courier or transportation service 13. The sample is then collected from the initial test sample location and is transported to the phage laboratory at the scheduled time. In other embodiments printing of the shipping label could be skipped if the sample is already marked or tagged with information to facilitate identification and shipping. For example a sample collection facility may print and apply a label with suitable details, and this can be directly used by a courier. In another embodiment the sample collection facility may apply an identification tag which contains unique identifying information to the patient sample, or the sample container may incorporate such an identification tag. The identification tag may be a printed barcode or QR code, or a wireless Radio Frequency (RF) tag such as near field or RFID tag, or other appropriate tag. This information can be provided to the phage treatment computing system 20 using the user interface, or an appropriate reading or scanning device associated with the computing device providing the user interface. This information can then be used to coordinate the transportation of the patient sample, such as by providing the information to the courier who can scan the identification tag at pickup.

Phage Laboratory

The patient sample is then received 34 at the designated phage laboratory 3o, and this is reported back to the phage treatment computing system 20 and logged into database 21. The patient sample is then tested and/or analyzed 35 and the results are provided to the phage treatment computing system 20 to identify a phage mixture treatment 26 comprising one or more phage with potential efficacy against bacteria in the patient sample. Testing and analysis of the patient sample may comprise growing samples of the patient samples and evaluating effectiveness of a plurality of candidate phages as outlined below. For example this may include performing assays to determine phage-host sensitivity (or resistance) profile of a bacterium in the patient sample. Similarly testing and analysis of the patient sample may comprise identifying the bacteria present in the patient sample. If the sample contains bacteria that are susceptible to infection by a given phage, then that phage can be included in the phage mixture treatment.

Determining the "bacterial host range" of a phage refers to the process of identifying the bacterial strains that are susceptible to infection by a given phage. The host range of a given phage is specific to a specific strain level. Screening to determine bacterial host range of a phage may be performed using conventional methods familiar to one of skill in the art (and as described in the examples), including but not limited to assays using robotics and other high-throughput methodologies.

Phage with a broad host range (e.g., capable of infecting greater than 10 bacterial strains) indicates, in general, that the receptor for said phage is common among the strains. A narrow host range (e.g., capable of infecting less than 5 bacterial strains) may indicate a unique receptor.

In some embodiments testing of a patient sample comprises determining a "phage-host sensitivity profile" of a bacterium and relies on the same type of assays used to analyze a bacterial host range of a phage. Here, the goal is to screen one bacterial strain against multiple different phage to classify those phage that are able to infect and/or lyse the bacterium (a "sensitive profile") vs. those phage that are unable to infect and/or lyse the bacterium (a "resistant profile").

In one embodiment, phages used to test patient sample and to generate treatments are prescreened to for undesirable, deleterious and/or toxic characteristics. The phage identified as having undesirable, deleterious and/or toxic characteristics are excluded from compositions used for testing and treatment. Examples of such undesirable, deleterious and/or toxic characteristics, include, but are not limited to: phage which carry toxin genes, phage which possess lysogenic properties and/or carry lysogeny genes, phage which can transduce bacterial virulence factor genes or antibiotic resistance genes different from factors already present in the patient, phage which carry any antibiotic-resistance genes or can confer antibiotic resistance to bacterial strains, and phage which elicit an antagonistic immune response and/or provoke a strong allergenic response in a mammalian system.

Examples of bactericidal activities that can be considered when creating a phage-host sensitivity profile include lysis, delay in bacterial growth, or a lack of appearance of phage-resistant bacterial growth. In further preferred embodiments, bactericidal activity can be measured by plaque assay. Data that can be derived from the plaque assay includes, but is not limited to: size, cloudiness and/or clarity of the plaque is measured and/or the presence of a halo around the plaque.

In further preferred embodiments, bactericidal activity can be measured by: (a) phage that can generate clear point plaques on the bacterial sample; (b) phage that demonstrate lytic characteristics using a rapid streak method on a plate; (c) bacterial lysis of at least 0.1, at least 0.2, at least 0.3, at least 0.4, at least 0.5, or between 0.1-0.5 OD600 absorbance difference in turbidity with small or large batch assays; (d) delay in bacterial growth of at least 0.1, at least 0.125, at least 0.15, at least 0.175, at least 0.2, or at between 0.1-0.2 OD600 absorbance difference in turbidity in bacteriostatic phage infections; (e) a lack of appearance of phage-resistant bacterial growth for at least 4 hours, at least 5 hours, at least 6 hours, at least 7 hours, or in between 4-6 hours post-infection; (f) reduced growth curves of surviving bacteria after phage infection for at least 4 hours, at least 5 hours, at least 6 hours, at least 7 hours, or in between 4-6 hours in the Host Range Quick Test; or (g) a prevention or delay of at least 50, at least 75, at least 100, at least 125, at least 150, at least 175, at least 200, or between 50-200 relative respiration units in tetrazolium dye-based color change from active bacterial metabolism using the Omnilog bioassay of phage-infected bacteria from the Host Range Quick Test.

Testing and analysis of the patient sample may also comprise identifying the bacteria present in the patient sample and comparing the similarity of this bacteria to bacteria that are known to be susceptible to infection by a given phage. If the same bacteria, or a highly similar bacteria is present in the patient sample then that phage can be included in the phage mixture treatment. Similarity may be assessed based on any clinical, genotypical and/or metabolic information obtained either from the treating physician (eg via patient records obtained via the user interface) or though experiments conducted at the treatment laboratory 30 including but not limited to, antibiotic resistance, ability to utilize various sugars, ability to utilize various carbon sources, ability to grow on various salts, ability to grow in presence or absence of oxygen, or bacterial motility.

Testing and analysis may also comprise sequencing the patient sample. This may involve performing bioinformatics or sequence analysis to identify candidate phages, as well as to build up database that may assist in later bioinformatics based analysis of subsequent samples (ie once treatment results are known). The bioinformatics analysis may comprise sequence analysis to search for sequences or motifs which are known to be associated with specific phage efficacy and these phages may then be prioritised for testing or treatment. Sequence analysis may also identify that the bacteria in the patient sample are similar to bacteria with known effective phage mixture treatments, and these phage may then be prioritised for testing or treatment.

Once a phage mixture treatment is identified 26, a report is produced detailing the proposed treatment and this is provided to the treating physician 17 via the user interface 10. The treating physician can then approval or authorize the proposed treatment 18 which enables the proposed treatment to be prepared and dispensed by a phage dispensing apparatus 40, such as a dispensing kiosk located at a patient treatment location such as a hospital or care facility where the patient is admitted, or at the treating physicians consulting rooms, or a phage laboratory 30 from where the dispensed phage mixture treatment can be transported to or provided to the patient.

Phage Dispensing Apparatus (Phage Kiosk)

The phage dispensing apparatus 40 is configured to receive a treatment request 42 and prepare a phage mixture dose for treating a patient.

Figure 2:
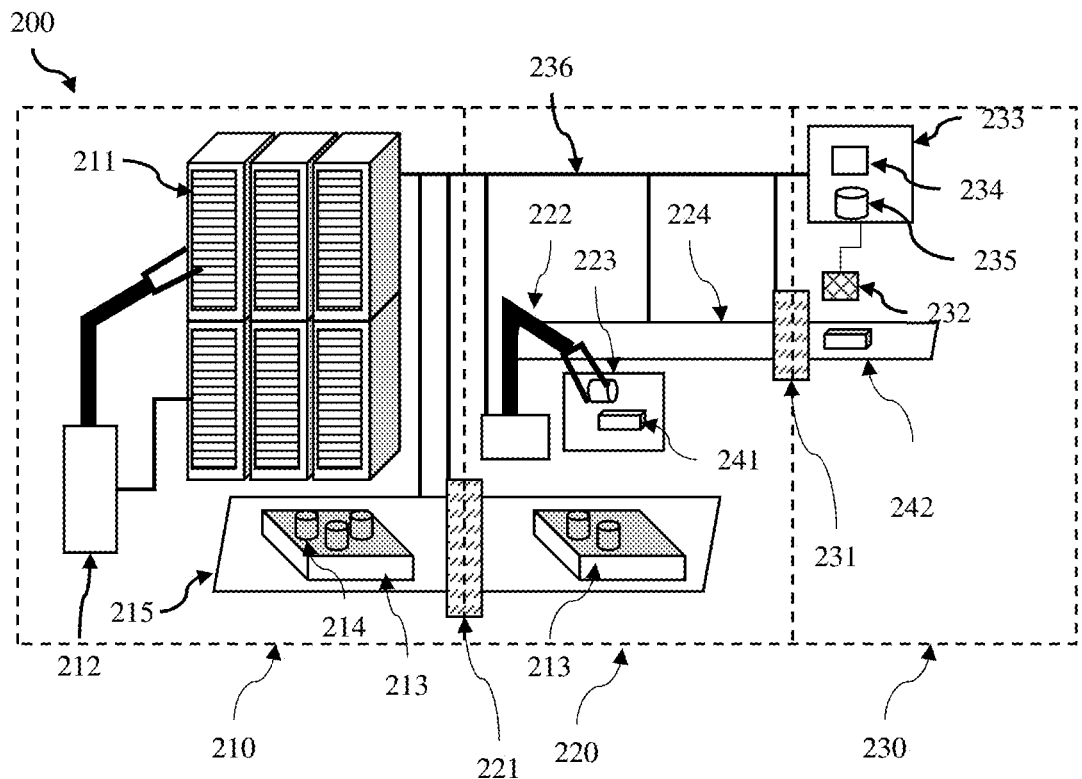
FIG. 2 is a schematic diagram of an embodiment of a Phage Dispensing apparatus according.

FIG. 2 is a schematic diagram of an embodiment of a Phage Dispensing apparatus. In this embodiment the phage dispensing apparatus is a kiosk 200 which integrates the components into a single unit. However, in other embodiments the phage dispensing apparatus 40 could be implemented in other configurations and comprise a plurality of components and may be spread across one or more rooms.

The phage dispensing apparatus 200 comprises a storage portion 210, a preparation portion 220 and a dispensing portion 230. A computing apparatus 233 comprises a control module 234 that executes on the computing apparatus and is configured to receive treatment requests and coordinates preparation and dispensing of one or more phage mixture doses 242 by the apparatus 200. One or more phage mixture doses can be prepared at the same time. The computing apparatus also provides a user interface that allows users to interact with the apparatus such as approve a treatment 18, check the progress of the preparation of a treatment, and authorize the dispensing of a prepared phage mixture dose (or doses). The computing apparatus is connected to various components of the system via wired or wireless links 236 to enable the control module to control operation of the various functional components. This may be to directly control components such as robotic arms, RFID readers, conveyors and doors, or to send control commands to local microcontrollers to actuate operation under local control.

In some embodiments the treatment request is the treatment approval or a message generated in response to the treating physician approving (or authorizing) treatment 18 via the user interface 10. In some embodiments the treatment request comprises dispensing information on the approved phage mixture treatment to enable the phage dispensing apparatus 40 to directly prepare and dispense one or more doses of the phage mixture treatment. In other embodiments the treatment request comprises identifying information that allows the phage dispensing apparatus 40 to request the dispensing information from the phage treatment computing system to enable the phage dispensing apparatus 40 to directly prepare and dispense one or more doses of the phage mixture treatment. In one embodiment a phage mixture treatment is assigned a unique treatment identifier by the phage treatment computing system 20. This unique identifier is included in the report to the treating physician and in the approval treatment request provided to the phage dispensing apparatus. The phage dispensing apparatus then sends this identifier to the phage treatment computing system to receive the information required to enable preparation and dispensing of the phage mixture treatment.

In some embodiments, when a phage mixture treatment is identified, the phage treatment computing system directly sends the phage mixture treatment dispensing information to enable the phage dispensing apparatus 40 to directly prepare and dispense one or more doses of the phage mixture treatment. In some embodiments the information includes the unique treatment identifier, and the treatment request includes the unique treatment identifier allowing the phage treatment computing system to look up the earlier received dispensing information. In some embodiments the phage mixture treatment information is sent to the phage dispensing apparatus 40 around the same time as the proposed treatment is provided to the treating physician 17. This enables more rapid dispensing as the dispensing apparatus can begin preparing the treatment as soon as the treatment request is received (e.g. as soon as approval is provided), and/or to perform any preparations to enable faster dispensing as soon as the treatment request is received.

The phage dispensing apparatus comprises stocks of a plurality of phages stored in vials or similar containers which can be sealed (e.g. ampules). Each vial contains one or more strains of purified phage, and the plurality of vials are stored or housed in a temperature controlled storage box or container. The phage stocks may comprise pre-filled single dose vials each with a single phage, prefilled single dose vials filled with a plurality of phages, pre-filled single dose vials filled with a specific phage mixture, or some combination. In some embodiments the single dose vials are ampules or other hermetically sealed containers. In other embodiments some or all of the vials may be multi-dose vials. In some embodiments the phage stocks are maintained in racking system 211 of a storage portion 210 which is kept at ultra low temperatures such as temperatures in the range of −40° C. to −90° C. In some embodiments the storage portion is substantially maintained at −80° C. or even at −90° C. In some embodiments the storage portion is an ultra low temperature freezer configured with an internal racking system 211. In some embodiments each vial (or ampule) contains a sterile-filled preparation with a volume of 1 ml to 50 ml. Each preparation comprises one or more strains of purified phage. In some embodiments each preparation comprises $10^6$ to $10^{14}$ plaque-forming unit (PFU) of one or more phages. The vials may be supplied as an ampule (eg a hermetically sealed vials) and contain endotoxin levels below FDA allowed levels for injection. The vials may also contain an identification tag.

The control module 234 within the phage dispensing apparatus controls retrieval of one or more phage vials 43 from the storage portion 210 and moves them to a preparation portion 220 using a robotic system or apparatus. In some embodiments an electronic catalogue or inventory system is used to track and/or monitor the stock levels and store the locations of the vials within the storage portion. As vials are removed from the phage stocks 41, the inventory is updated 44, and if low stock of a particular phage is identified, then a request for new stock 45 is sent to a supplier, such as a phage laboratory 30. When new phage stock arrives this is loaded into the storage portion and the inventory updated. One or more sensors, or example located at a door or entry to the storage box 210 may be used to detect addition and removal of each vial to and from the storage box 210 using the identification tag. For example the sensor may be an RFID reader or barcode scanner. The catalogue system may also be configured to record or store the location of each vial within the storage box 210, for example a bay number and/or a row and column address in a racking system.

In one embodiment the storage portion or freezer 210 is configured as a series of racks or bays 211 and a robotic apparatus 212, such as a selector arm is configured to remove selected vials from the appropriate rack address or bay and place vials 214 in a tray 213 on a conveyor belt 215 that spans the storage portion 210 and preparation portion 220. A door 221 such as a sliding door separates the storage portion 210 from the preparation portion 220. When all required samples have been removed from the freezer 211 by the robotic selector arm and placed in the tray 213 then the door 221 is opened and the conveyor 215 is operated to move the tray 213 into the preparation portion 220. Various robotic configurations can be used to implement this functionality. For example, each bay could be configured as a box like space rectangular space with a width matching the diameter of a single vial and robotically controlled front gate and a moveable rear panel. The vials are stored single file in the bay and dispensed by opening the front gate and pushing the vials from the rear until the forward most vial is pushed out of the bay. This could be pushed into the arms of a robotic gripper, or placed on a conveyor or a moveable tray. Loading is the reverse operation. Using the known size of vials the location of the rear panel (or rear pusher) can be used to indicate the number of vials stored in the bay. In another embodiment, the bay could comprise a tray with location formations to receive and support a fixed number of vials (e.g. a 5×2 array). Loading and unloading could be performed by complete removal of the tray and movement to a loading area, or by the tray could be configured to extend (and later retract) from the bay to enable a robotic selector arm to place and remove vials in the tray from the location formations. Various mechanisms can be used to track which location formations are empty or filled such as sensor within each location formation (ie indicating presence or absence). Alternatively, the robotic selector could include a scanner which attempts to detect or read the identification tag of a vial in a specific location. Other techniques such as computer vision techniques that capture and process an image to determine occupied locations.

The retrieved phage vials are moved from the conveyor 215 to a preparation table 223 where any frozen vials are allowed to defrost (if necessary) and are then mixed. In some embodiments the preparation portion is a refrigerated portion maintained at temperature between 4° C. and −10° C. In preferred embodiments, defrosting of vials may be through natural convection due to the temperature difference between the storage portion 210 and the preparation portion 220, or the vials may be placed in a bath or other suitable defrosting container to assist in more rapid defrosting of the vial. The contents of any single dose vials are emptied into a preparation container 241 on the preparation table 223 and mixed along with any other inactive ingredients selected from a variety of conventional pharmaceutically acceptable excipients, carriers, buffers, and/or diluents. A robotic apparatus such as one or more robotic arms 222 move vials within the preparation portion to control the mixing and preparation of doses. In some embodiments the preparation container 241 is the dispensing container 242 and the entire contents represent the phage mixture dose. In other embodiments the entire contents or a predefined amount are transferred to a dispensing container to generate a phage mixture dose 242.

Once the resultant phage mixture dose is prepared an alert is generated that a dose of the phage mixture is ready to be dispensed. This may be sent to one or more persons such as one or more clinician involved in treating the patient such as a pharmacist, nurse and/or the treating physician. An authorized user such as a pharmacist that received the alert provides authentication credentials to a user interface of the dispensing apparatus, and the phage mixture dose is dispensed in the dispensing container 48. This phage mixture dose is then used to treat the patient. Dispensing may comprise a robotic arm 222 placing the prepared phage mixture dose 242 in a dispensing container onto a conveyor 224. A door 231 separates the preparation portion 220 from the dispensing portion 230. The door 231 is opened and conveyor is operated to move and dispense the prepared phage mixture dose in dispensing container 242. A reader, such as an RFID reader registers an identifier of the dispensing container 242.

In some embodiments the effectiveness of the treatment is reported 49 to the phage treatment computing system to assist in identifying phage mixture treatments for future patients. This effectiveness may be a binary assessment by the treating clinician such as effective or not effective, or more detailed medical history may be provided including test results and observations to document the patient response. Such information can then be integrated into machine learning or other assessment systems to assist in identifying phage treatments for future patients, or to monitor safety and efficacy.

In one embodiment the racking system 211 is configured to store hundreds, or thousands or tens of thousands single does phage vials. In one embodiment the racking system is divided into a multiplicity of bays, where each bay stores a plurality of samples of a specific single dose phage vial. For example, the system may be configured as 600 bays (for example in 24×25 matrix or 50×12 matrix), each storing 10 identical single dose phage vials, giving a system capacity of 6000 single doses. Additionally, the system may store a plurality of pre-mixed/prepared phage treatment mixtures, each containing a plurality of phages to target specific bacterial pathogens. For example, the system could store 20 vials of pre-mixed/prepared phage treatment mixtures for each of six leading multi-drug resistant (MDR) pathogenic bacteria. These pre-mixed/prepared phage treatment mixtures can thus be immediately dispensed once a patient is identified as having being infected with one of these MDR pathogenic bacteria.

Various robotic systems may be used to move vials and materials around the phage dispensing apparatus. These may comprise robotic arms, XY and XYZ platforms, conveyors, pickers, grippers, etc. The rack may be a robotic rack with computer selectable bays.

Each vial 214 in the storage portion may be provided with a bar code or RFID tag for identification and tracking purposes. RFID readers may be located at various strategic points in the sample apparatus. For example, a scanner may be placed adjacent conveyor 215 so that each vial is scanned as it removed from the storage rack 211 and is placed in tray 213. The ID is then provided to the control module 234 (via communication link 236) to update the inventory and initiate ordering as required. Similarly a reader may be placed adjacent the preparation table 223 to record emptying of vials 214. Further the dispensing container 242 may be provided with a bar code or RFID tag which is scanned by reader 232 when dispensing.

The dispensing kiosk can be housed in a relatively compact unit such as the size of a large freezer or refrigerator unit (eg several cubic metres) allowing installation in a large number of hospital pharmacies or treatment centres to enable rapid treatment once a suitable phage mixture treatment is identified. A distributed or cloud based phage treatment computing system 20 allows treating physicians and clinicians to log into the system and rapidly arrange phage based treatments for patients. Once testing of a patient sample is performed (which can take 24-48 hours) the results are rapidly provided to the treating physician and/or the phage dispensing apparatus to facilitate rapid treatment of the patient.

Compositions and Methods of Treatment

In another aspect, the instant invention relates to compositions ("mixtures") comprising phage (including a mixture of phage) identified in the process described as Block 26. In a particular embodiment, the compositions are therapeutically effective phage mixtures of very high titer and purity which are not found in nature.

As understood by one of skill in the art, the type and amount of pharmaceutically acceptable additional components included in the pharmaceutical compositions may vary, e.g., depending upon the desired route of administration and desired physical state, solubility, stability, and rate of in vivo release of the composition.

As contemplated herein, the phage mixtures, and particularly pharmaceutical compositions of the phage mixtures, comprise an amount of phage in a unit of weight or volume suitable for administration to a subject. The volume of the composition administered to a subject (dosage unit) will depend on the method of administration and is discernible by one of skill in the art. For example, in the case of an injectable, the volume administered typically may be between 0.1 and 1.0 ml, e.g., approximately 0.5 ml, with a maximal permissible level of endotoxin in injected products is 5 EU/kg/hour or 350 EU/hour in a 70 kg person.

For administration by intravenous, cutaneous, subcutaneous, or other injection, a pharmaceutical formulation is typically in the form of a parenterally acceptable aqueous solution of suitable pH and stability, and may contain an isotonic vehicle as well as pharmaceutical acceptable stabilizers, preservatives, buffers, antioxidants, or other additives familiar to one of skill in the art.

Methods of Treatment

The phage mixtures generated according to the methods of the invention can be used to treat a bacterial infection in a subject or bacterial contamination in the environment. Such methods of treatment include administering to a subject in need thereof an effective amount of a dose of a phage mixture treatment generated according to the method described herein.

It will be appreciated that appropriate dosages of the active compounds or agents can vary from patient to patient. Determining the optimal dosage will generally involve the balancing of the level of therapeutic benefit against any risk or deleterious side effects of the administration. The selected dosage level will depend on a variety of factors including, but not limited to, the route of administration, the time of administration, the rate of excretion of the active compound, other drugs, compounds, and/or materials used in combination, and the age, sex, weight, condition, general health, and prior medical history of the patient. The number of active compounds and route of administration will ultimately be at the discretion of the physician, although generally the dosage will be to achieve concentrations of the active compound at a site of therapy without causing substantial harmful or deleterious side-effects.

In general, a suitable dose of the active compound or agent is in the range of about about 1 µg or less to about 100 µg or more per kg body weight. As a general guide, a suitable amount of a dose of a phage mixture generated according to the method described herein can be an amount between from about 0.1 µg to about 10 mg per dosage amount.

In addition, a dose of a phage mixture can be administered in a variety of dosage forms. These include, e.g., liquid preparations and suspensions, including, preparations for parenteral, subcutaneous, intradermal, intramuscular, intraperitoneal, intra-nasal (e.g., aerosol) or intravenous administration (e.g., injectable administration), such as sterile isotonic aqueous solutions, suspensions, emulsions or viscous compositions that may be buffered to a selected pH. In a particular embodiment, it is contemplated herein that the phage mixture is administered to a subject as an injectable, including but not limited to injectable compositions for delivery by intramuscular, intravenous, subcutaneous, or transdermal injection. Such compositions may be formulated using a variety of pharmaceutical excipients, carriers or diluents familiar to one of skill in the art.

In another particular embodiment, a dose of the phage mixture may be administered orally. Oral formulations for administration according to the methods of the present invention may include a variety of dosage forms, e.g., solutions, powders, suspensions, tablets, pills, capsules, caplets, sustained release formulations, or preparations which are time-released or which have a liquid filling, e.g., gelatin covered liquid, whereby the gelatin is dissolved in the stomach for delivery to the gut. Such formulations may include a variety of pharmaceutically acceptable excipients described herein, including but not limited to mannitol, lactose, starch, magnesium stearate, sodium saccharine, cellulose, and magnesium carbonate.

In a particular embodiment, it is contemplated herein that a composition for oral administration may be a liquid formulation. Such formulations may comprise a pharmaceutically acceptable thickening agent which can create a composition with enhanced viscosity which facilitates mucosal delivery of the active agent, e.g., by providing extended contact with the lining of the stomach. Such viscous compositions may be made by one of skill in the art employing conventional methods and employing pharmaceutical excipients and reagents, e.g., methylcellulose, xanthan gum, carboxymethyl cellulose, hydroxypropyl cellulose, and carbomer.

Other dosage forms suitable for nasal or respiratory (mucosal) administration, e.g., in the form of a squeeze spray dispenser, pump dispenser or aerosol dispenser, are contemplated herein. Dosage forms suitable for rectal or vaginal delivery are also contemplated herein. The constructs, conjugates, and compositions may also be lyophilized and may be delivered to a subject with or without rehydration using conventional methods.

As understood herein, the methods of administering a phage mixture described herein to a subject can occur via different regimens, i.e., in an amount and in a manner and for a time sufficient to provide a clinically meaningful benefit to the subject. Suitable administration regimens for use with the instant invention may be determined by one of skill in the art according to conventional methods. For example, it is contemplated herein that an effective amount may be administered to a subject as a single dose, a series of multiple doses administered over a period of days, or a single dose followed by a boosting dose thereafter.

The administrative regimen, e.g., the quantity to be administered, the number of treatments, and effective amount per unit dose, etc. will depend on the judgment of the practitioner and are subject dependent. Factors to be considered in this regard include physical and clinical state of the subject, route of administration, intended goal of treatment, as well as the potency, stability, and toxicity of the phage mixture. As understood by one of skill in the art, a "boosting dose" may comprise the same dosage amount as the initial dosage, or a different dosage amount. Indeed, when a series of doses are administered in order to produce a desired response in the subject, one of skill in the art will appreciate that in that case, an "effective amount" may encompass more than one administered dosage amount.

Although the invention herein has been described with reference to embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

Computing System

Figure 3:
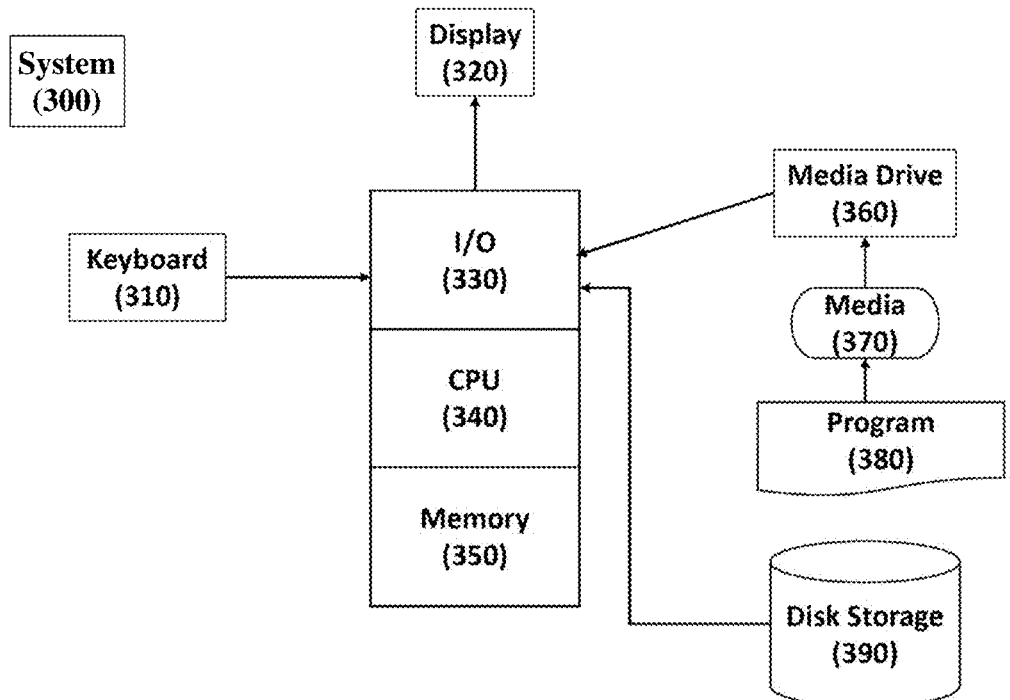
FIG. 3 is schematic diagram of a computing apparatus according to an embodiment.

FIG. 3 depicts an exemplary computing system configured to perform any one of the computer implemented processes described herein. In this context, the computing system may include, for example, a processor, memory, storage, and input/output devices (e.g., monitor, keyboard, disk drive, Internet connection, etc.). However, the computing system may include circuitry or other specialized hardware for carrying out some or all aspects of the processes. The computer system may be a distributed system including cloud based computing systems. In some operational settings, the computing system may be configured as a system that includes one or more units, each of which is configured to carry out some aspects of the processes either in software, hardware, or some combination thereof. For example, the user interface may be provided on a desktop computer or tablet computer, whilst the phage treatment computing system 20 may be a server based system. The phage dispensing kiosk may comprise microcontroller or microprocessor based subsystems for controlling robotic arms, conveyors, and scanners as well as a desktop computing system to provide a user interface and communicate with the database 21 in the phage treatment computing system 20.

Those of skill in the art would further appreciate that the various illustrative logical blocks, modules, circuits, and algorithm steps described in connection with the embodiments disclosed herein may be implemented as electronic hardware, computer software or instructions, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. For a hardware implementation, processing may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. Software modules, also known as computer programs, computer codes, or instructions, may contain a number a number of source code or object code segments or instructions, and may reside in any computer readable medium such as a RAM memory, flash memory, ROM memory, EPROM memory, registers, hard disk, a removable disk, a CD-ROM, a DVD-ROM, a Blu-ray disc, or any other form of computer readable medium. In some aspects the computer-readable media may comprise non-transitory computer-readable media (e.g., tangible media). In another aspect, the computer readable medium may be integral to the processor. The processor and the computer readable medium may reside in an ASIC or related device. The software codes may be stored in a memory unit and the processor may be configured to execute them. The memory unit may be implemented within the processor or external to the processor, in which case it can be communicatively coupled to the processor via various means as is known in the art.

Specifically, FIG. 3 depicts computing system (300) with a number of components that may be used to perform the processes described herein. For example, an input/output ("I/O") interface 330, one or more central processing units ("CPU") (340), and a memory section (350). The I/O interface (330) is connected to input and output devices such as a display (320), a keyboard (310), a disk storage unit (390), and a media drive unit (360). The media drive unit (360) can read/write a computer-readable medium (370), which can contain programs (380) and/or data. The I/O interface may comprise a network interface and/or communications module for communicating with an equivalent communications module in another device using a pre-defined communications protocol (e.g. Bluetooth, Zigbee, IEEE 802.15, IEEE 802.11, TCP/IP, UDP, etc).

At least some values based on the results of the processes described herein can be saved for subsequent use. Additionally, a non-transitory computer-readable medium can be used to store (e.g., tangibly embody) one or more computer programs for performing any one of the above-described processes by means of a computer. The computer program may be written, for example, in a general-purpose programming language (e.g., Pascal, C, C++, Java, Python, JSON, etc.) or some specialized application-specific language.

Also provided is a non-transitory computer-readable storage medium comprising computer-executable instructions for carrying out any of the methods described herein. Further provided is a computer system comprising one or more processors, memory, and one or more programs, wherein the one or more programs are stored in the memory and configured to be executed by the one or more processors, the one or more programs including instructions for carrying out any of the methods described herein.

Those of skill in the art would understand that information and signals may be represented using any of a variety of technologies and techniques. For example, data, instructions, commands, information, signals, bits, symbols, and chips may be referenced throughout the above description may be represented by voltages, currents, electromagnetic waves, magnetic fields or particles, optical fields or particles, or any combination thereof.

EXAMPLES

The invention will now be further illustrated with reference to the following examples. It will be appreciated that what follows is by way of example only and that modifications to detail may be made while still falling within the scope of the invention.

Example 1: Phage Isolation/Characterization from Environmental Sources

Powdered TSB medium (Becton, Dickinson and Company) can be mixed with raw sewage to a final concentration of 3% w/v. Different bacterial strains can be grown to exponential phase, and 1 mL of each strain added to 100 mL aliquots of TSB-sewage mixture, and incubated at 37° C. and 250 rpm overnight. The following day, 1 mL of the infected TSB-sewage mixture is harvested and centrifuged at 8,000×g for 5 min to pellet cells and debris. The supernatant is transferred to a sterile 0.22 µm Spin-X® centrifuge tube filter (Corning, NY), and centrifuged at 6,000×g to remove any remaining bacteria. A 10 µL aliquot of the filtrate is mixed with 100 µL of exponential growth culture of the bacterial strain, incubated at 37° C. for 20 min, mixed with 2.5 mL of molten top agar (0.6% agar) tempered to 50° C., and poured over TSB agar plates (1.5% TSB agar). Plates are incubated overnight at 37° C., and subsequent phage plaques are individually harvested and purified three times on appropriate bacterial strain isolates using the standard procedures described by, for example, Sambrook et al.

If desired, high-titer phage stocks can be propagated and amplified in corresponding host bacteria by standard procedures known to the skilled artisan. Large-scale phage preparations can be purified by caesium chloride density centrifugation, and filtered through a 0.22 µm filter (Millipore Corporation, Billerica, MA).

For example, phage can be purified by Caesium chloride gradient as is well known in the art. Here, the generated purified phage suspension (1 ml) can be precipitated with 10% polyethylene glycol 8000 (Sigma-Aldrich) and 0.5 M sodium chloride at 40 C overnight. Subsequently, the suspension can be centrifuged at 17,700 g for 15 minutes and the supernatant removed. Alternatively, the phage suspension can be dialyzed. The PEG/salt-induced precipitate is resuspended in 0.5 ml of TE buffer (pH 9.0) and treated with 20 ul of 20 mg/ml proteinase K for 20 minutes at 560 C followed by treatment with SDS at a final concentration of 2% at 650 C for 20 minutes. This mixture is then phenol/chloroform (25:24:1 phenol:chloroform:isoamyl alcohol, Sigma Aldrich) treated at least twice and the aqueous phase is then precipitated with 2.5 volumes of ice cold 96% ethanol and 0.1 volume of sodium acetate (pH 4.8). Subsequent to centrifugation, the pellet is washed in 70% ethanol and resuspended in 100 ul of TE buffer (pH 8.0). Phage stocks can then be stored at 4° C. indefinitely. Phage titer can be assessed by plating ten-fold serial dilutions and calculating the plaque forming units (PFU).

Other methods of phage purification include, but are not limited to partition separations with either octanol or butanol. In this technique, phage normally stay in the aqueous phase while endotoxins tend to be absorbed by the alcohol phase.

Example 2: Assays Used to Generate Phage-Host Sensitivity Profiles

To carry out the disclosed method, the genomes of multiple different bacterial strains having similar or identical phage-host sensitivity profiles need to be compared. If a phage-host sensitivity profile of a bacterium is already known, the following assays do not need to be performed. However, if the phage-host sensitivity profile of a bacterium is unknown, any of the following assays can be used to determine or experimentally derive such a profile.

One method of determining a sensitivity/resistant profile of a bacterium relies on an automated, indirect, liquid lysis assay. Briefly, an overnight culture of a bacterial strain is inoculated into the wells of a 96-well plate containing TSB mixed with 1% v/v tetrazolium dye. Phage are then added to each well, and plates were incubated in an OmniLog™ system (Biolog, InC, Hayward, CA) at 37° C. overnight. See, Henry, Bacteriophage 2:3, 159-167 (2012). The tetrazolium dye indirectly measures the respiration of the bacterial cells. Respiration causes reduction of the tetrazolium dye, resulting in a color change to purple. The color intensity of each well is quantified as relative units of bacterial growth. For host range determination, bacteria are inoculated at 105 colony forming units (CFU) per well and phage are added at a concentration of 106 plaque forming units (PFU) per well for an MOI of 10. For mixture synergy studies, bacteria can be inoculated at 106 CFU per well and phage added at a concentration of 108 PFU per well for an MOI of 100.

A second assay can also be used to determine the sensitivity/resistant profile of a bacterium. In this assay, a dilution series spot plate assay is used to observe plaque formation. Specifically, 50 µL of an overnight culture of a bacterium is used to individually inoculate 5 mL of molten top agar tempered to 55° C. The inoculated agar is then mixed thoroughly by brief vortexing and then spread over square LB agar plates. Top agar is allowed to set for approximately 45 min, at which time 4 µL aliquots of 1010 to 102 PFU in 10-fold dilutions of each phage are spotted on the surface. Spots are allowed to fully absorb into the top agar, after which plates were incubated at 37° C. for 24 hours. Plaque formation can then be assessed.

Time-kill experiments can also be used to provide a quantitative sensitivity/resistant profile of a bacterium. Here, an overnight culture of a bacterium is diluted 1:1000 in fresh LB broth to a final concentration of approximately $1 \times 10^6$ CFU per mL. Twenty mL aliquots are then transferred to 250 mL Erlenmeyer flasks and incubated at 37° C. with shaking at 200 rpm for 2 hours. Samples are then challenged with either $2 \times 10^{11}$ PFU per mL of a phage or an equal volume of sterile phosphate buffered saline (PBS) and returned to incubation. One hundred µl aliquots are taken at 0, 2, 4, and 24 hours, serially diluted in PBS, and plated on LB agar. Plates are incubated at 37° C. for 24 hours and plaque formation is evaluated.

Changes in a bacterium due to phage exposure can also be monitored using Raman spectroscopy. Here, each sample is obtained from LB agar plates and are directly transferred into a disposable weigh dish for spectral collection. Raman spectra can be collected using an 830 nm Raman PhA T system (Kaiser Optical Systems, InC, Ann Arbor, MI, USA). Spectra are collected using a 3 mm spot size lens with 100 sec total acquisition time and 1 mm spot size lens with 100 sec total acquisition time for time-kill assay samples. Spectra are then preprocessed by baseline removal using a sixth order polynomial and intensity normalization to the 1445 cm-1 Raman vibrational band prior to analysis.

Other examples of bactericidal activities that can be considered when creating a sensitivity/resistant profile include lysis, delay in bacterial growth, or a lack of appearance of phage-resistant bacterial growth. In further preferred embodiments, bactericidal activity can be measured by: (a) phage that can generate clear point plaques on the bacterial sample; (b) phage that demonstrate lytic characteristics using a rapid streak method on a plate; (c) bacterial lysis of at least 0.1, at least 0.2, at least 0.3, at least 0.4, at least 0.5, or between 0.1-0.5 OD600 absorbance difference in turbidity with small or large batch assays; (d) delay in bacterial growth of at least 0.1, at least 0.125, at least 0.15, at least 0.175, at least 0.2, or at between 0.1-0.2 OD600 absorbance difference in turbidity in bacteriostatic phage infections; (e) a lack of appearance of phage-resistant bacterial growth for at least 4 hours, at least 5 hours, at least 6 hours, at least 7 hours, or in between 4-6 hours post-infection; (f) reduced growth curves of surviving bacteria after phage infection for at least 4 hours, at least 5 hours, at least 6 hours, at least 7hours, or in between 4-6 hours in the Host Range Quick Test; or (g) a prevention or delay of at least 50, at least 75, at least 100, at least 125, at least 150, at least 175, at least 200, or between 50-200 relative respiration units in tetrazolium dye-based color change from active bacterial metabolism using the Omnilog bioassay of phage-infected bacteria from the Host Range Quick Test.

Using these assays, one can test multiple phage against a diverse set of bacterial strains to create a phage-host sensitivity profile. This profile can be based on both the ability of the phage to infect a bacterium, and also could be based, for example, on the number of hours each phage could prevent growth of the bacterial host in liquid (hold time) and/or the clarity/turbidity of the plaque. Once a phage-host sensitivity profile is experimentally generated for multiple bacterial strains, the strains can be categorized into groups exhibiting similar profiles, and this information can be used to speed up identification a phage mixture treatment for a new patient sample, such as by identification similarities between bacteria in the patient sample and bacteria from one of the groups.

Example 3: Genome Sequencing, Assembly & Annotation

Phage and bacteria genomes can be sequenced using standard sequencing techniques and assembled using contig analysis as is well known in the art. For example, 5 ug of DNA isolated from phage or bacteria can be extracted and shipped to a contract sequencing facility. A 40- to 65-fold sequencing coverage is obtained using pyrosequencing technology on a 454 FLX instrument. The files generated by the 454 FLX instrument are assembled with GS assembler (454, Branford, Conn.) to generate a consensus sequence. Quality improvement of the genome sequence can involve sequencing of 15-25 PCR products across the entire genomes to ensure correct assembly, double stranding and the resolution of any remaining base-conflicts occurring within homopolynucleotide tracts. Protein-encoding open reading frames (ORFs) can be predicted using standard programs known in the art (such as BLASTP) followed by manual assessment and, where necessary, correction.

Genomic sequencing information can be used to speed up identification of a phage mixture treatment for a new patient sample. Sequencing encompasses both complete sequencing of the entire bacterium/phage genome or the sequencing of key regions of interest that have been identified as part of a predictive pattern, or sequencing of specific regions. These regions may be large regions (eg 50-90%) or specific target regions such as gene encoding regions or previously identified predictive regions (eg associated with phage efficacy). For example, if the bacteria in the patient sample matches bacteria for which an effective phage mixture treatment is known, for example through previous testing or treatment, then that phage mixture treatment could be tested against the patient sample or proposed as the phage mixture treatment. Similarly, one or more bacterial sequences (or sequence motifs) may be associated with an effective phage mixture treatment. In this case the patient sample could be sequenced and then searched for the associated sequence motifs. This phage mixture treatment could then be tested against the patient sample or proposed as the phage mixture treatment, or otherwise used in the decision making process. Such bioinformatics based methods do not rely on cell culture and therefore, can be carried out rapidly to either identify potential phages for testing or as proposed treatments providing subjects with much needed therapies in a more rapid fashion.

The invention is not limited to the embodiment hereinbefore described which may be varied in construction and detail without departing from the spirit of the invention. The entire teachings of any patents, patent applications or other publications referred to herein are incorporated by reference herein as if fully set forth herein.

What is claimed:

1. A phage dispensing apparatus comprising:
a computing apparatus comprising one or more processors, a memory, and one or more programs, wherein the one or more programs are stored in the memory and confiured to be executed by the one or more processors, the one or more programs are configured to cause the one or more processors to receive information over a network from a remote computing device regarding a patient and a phage mixture treatment for the patient specifying one or more phages based on a phage-host sensitivity profile;
a storage portion comprising a plurality of vials containing different phages, wherein each vial contains at least one phage;
a dispensing portion; and
one or more robotic systems controlled by the computing apparatus and configured to remove one or more vials containing the one or more phages specified by the phage mixture treatment from the storage portion to the dispensing portion to dispense one or more pharmaceutically acceptable doses of the phage mixture treatment, wherein the computing apparatus, storage portion, dispensing portion, and one or more robotic systems are at a treatment location of the patient.

2. The phage dispensing apparatus as claimed in claim 1, wherein the storage portion comprises a plurality of phage vials and the storage portion is kept at between −40 C and −90 C.

3. The phage dispensing apparatus of claim 2, wherein the phage mixture treatment comprises one type of phage.

4. The phage dispensing apparatus of claim 2, wherein the phage mixture treatment comprises more than one type of phage.

5. The phage dispensing apparatus as claimed in claim 1, wherein the computing apparatus is configured to maintain an inventory of the plurality of vials in the storage portion, and a sensor is configured to detect removal of a vial from the storage portion, and on detection the inventory is updated, and when an inventory level of a stored phage is less than a threshold amount, a request for new phage stock is transmitted to a supplier via a communications interface.

6. The phage dispensing apparatus of claim 5, wherein the phage mixture treatment comprises one type of phage.

7. The phage dispensing apparatus of claim 5, wherein the phage mixture treatment comprises more than one type of phage.

8. The phage dispensing apparatus as claimed in claim 1, wherein the computing apparatus monitors preparation of the one or more doses of the phage mixture treatment, and an alert is generated by a communications interface when the one or more doses of the phage mixture treatment is prepared and ready for dispensing, and the computing apparatus stores a database of authorized users, and is configured to only dispense the one or more doses of the phage mixture treatment to an authorized user.

9. The phage dispensing apparatus of claim 8, wherein the phage mixture treatment comprises one type of phage.

10. The phage dispensing apparatus of claim 8, wherein the phage mixture treatment comprises more than one type of phage.

11. The phage dispensing apparatus as claimed in claim 1, wherein the storage portion further comprises a plurality of pre-prepared phage mixture treatment vials comprising multiple phages with efficacy against one of a selected group of multi drug resistant bacteria, and preparing one or more doses of the phage mixture treatment comprises selecting one or more pre-prepared phage mixture treatment vials from the storage portion and optionally defrosting the selected one or more pre-prepared phage mixture treatment vials.

12. The phage dispensing apparatus of claim 11, wherein the phage mixture treatment comprises one type of phage.

13. The phage dispensing apparatus of claim 11, wherein the phage mixture treatment comprises more than one type of phage.

14. The phage dispensing apparatus as claimed in claim 1, wherein the phage dispensing apparatus further comprises a preparation portion, wherein the robotic systems move the one or more vials from the storage portion to the preparation portion to mix the one or more vials to generate a pharmaceutically acceptable phage mixture treatment, and then moves the pharmaceutically acceptable phage mixture treatment to the dispensing portion.

15. The phage dispensing apparatus of claim 14, wherein the phage mixture treatment comprises one type of phage.

16. The phage dispensing apparatus of claim 14, wherein the phage mixture treatment comprises more than one type of phage.

17. The phage dispensing apparatus as claimed in claim 1, further comprising:
a temperature controlled storage box containing a plurality of sealed vials each of which contains a sterile-filled preparation with a volume of between 1 ml and 50 ml, and each preparation comprises one or more strains of purified phage; and
an electronic catalogue apparatus configured to track inventory of the plurality of vials stored in the temperature controlled storage box.

18. The phage dispensing apparatus as claimed in claim 17, wherein each preparation comprises $10^6$ to $10^{14}$ plaque-forming unit (PFU) of one or more phages.

19. The phage dispensing apparatus as claimed in claim 18, wherein each vial is an ampule.

20. The phage dispensing apparatus as claimed in claim 17, wherein each vial comprises an identification tag, and the electronic catalogue apparatus comprises one or more sensors to detect addition and removal of each vial to and from the temperature controlled storage box using the identification tag, and is further configured to record a location of each vial within the temperature controlled storage box.

21. The phage dispensing apparatus as claimed in claim 20, wherein the electronic catalogue apparatus further comprises a robotic apparatus configured to move a vial to and from a storage location within the temperature controlled storage box.

22. A phage dispensing apparatus as claimed in claim 1, further comprising:
a computer apparatus comprising one or more second processors, a second memory, and one or more second programs, wherein the one or more programs are stored in the second memory and configured to be executed by the one or more second processors, the one or more second programs are configured to cause the one or more second processors to:
receive information regarding a patient sample via a user interface, the information regarding the patient sample comprising a patient sample location, a patient identifier, and a treatment location;
arrange transportation of the patient sample to a phage testing laboratory using the received information regarding the patient sample;
receive one or more test and/or analysis results from the phage testing laboratory and generate the phage mixture treatment comprising one of more phages from the phage testing laboratory;
send the phage mixture treatment and the patient identifier to the computing apparatus of the phage dispensing apparatus for dispensing the one or more doses of the phage mixture treatment.

23. The phage dispensing apparatus of claim 1, wherein the phage mixture treatment comprises one type of phage.

24. The phage dispensing apparatus of claim 1, wherein the phage mixture treatment comprises more than one type of phage.

25. The phage dispensing apparatus of claim 1, wherein the one or more programs are further configured to cause the one or more processors to:
monitor preparation of the phage mixture treatment and generate an alert when the one or more doses of the phage mixture treatment are ready for dispensing;
authorize a user receiving the alert based on received user credentials; and
in response to authorizing the user, control the one or more robotic systems to move the one or more doses to the dispensing portion to dispense the one or more doses of the phage mixture treatment.

26. A phage dispensing apparatus comprising:
a computing apparatus comprising one or more processors, a memory, and one or more programs, wherein the one or more programs are stored in the memory and configured to be executed by the one or more processors, the one or more programs are configured to cause the one or more processors to receive information regarding a patient and a phage mixture treatment for the patient based on a phage-host sensitivity profile;
a storage portion comprising a plurality of vials containing different phages, wherein each vial contains at least one phage;
a dispensing portion; and
one or more robotic systems controlled by the computing apparatus and configured to remove one or more vials containing phage for the phage mixture treatment from the storage portion to the dispensing portion to dispense one or more pharmaceutically acceptable doses of the phage mixture treatment, wherein the one or more programs are further configured to cause the one or more processors to:
control the one or more robotic systems to remove plural vials from the storage portion having different phages for the phage mixture treatment to a preparation portion to prepare the phage mixture treatment using the different phages of the plural vials.

27. The method of dispensing a phage mixture treatment from a phage dispensing apparatus comprising:
receiving by a computing apparatus information over a network from a remote computing device regarding a patient and a phage mixture treatment for the patient specifying one or more phages based on a phage-host sensitivity profile;
storing a plurality of vials containing different phages in a storage portion of the phage dispensing apparatus, wherein each vial contains at least one phage; and
controlling by the computing apparatus one or more robotic systems to remove one or more vials containing the one or more phages specified by the phage mixture treatment from the storage portion to a dispensing portion of the phage dispensing apparatus to dispense one or more pharmaceutically acceptable doses of the phage mixture treatment, wherein the computing apparatus, storage portion, dispensing portion, and one or more robotic systems are at a treatment location of the patient.

28. The method of claim 27, further comprising:
receiving information regarding a patient sample via a user interface of a computer apparatus, the information regarding the patient sample comprising a patient sample location, a patient identifier, and a treatment location;
arranging transportation of the patient sample to a phage testing laboratory using the received information regarding the patient sample;
receiving one or more test and/or analysis results from the phage testing laboratory and generating the phage mixture treatment comprising one or more phages from the phage testing laboratory;
sending the phage mixture treatment and the patient identifier to the computing apparatus of the phage dispensing apparatus to dispense the one or more doses of the phage mixture treatment.

* * * * *

UNITED STATES PATENT AND TRADEMARK OFFICE
CERTIFICATE OF CORRECTION

| | |
|---|---|
| PATENT NO. | : 11,911,345 B2 |
| APPLICATION NO. | : 16/896718 |
| DATED | : February 27, 2024 |
| INVENTOR(S) | : Carl Merril et al. |

It is certified that error appears in the above-identified patent and that said Letters Patent is hereby corrected as shown below:

In the Claims

Claim 1, Column 24, Line 26, replace "confiured to be executed by the one or more processors," with --configured to be executed by the one or more processors,--

Signed and Sealed this
Twenty-sixth Day of March, 2024

Katherine Kelly Vidal
Director of the United States Patent and Trademark Office